(12) United States Patent
O'Connell et al.

(10) Patent No.: US 7,005,653 B1
(45) Date of Patent: Feb. 28, 2006

(54) NEAR-FIELD INTRA-CELLULAR APERTURELESS TOMOGRAPHIC IMAGING

(75) Inventors: Daniel G. O'Connell, Oro Valley, AZ (US); Caitlin E. O'Connell-Rodwell, Menlo Park, CA (US)

(73) Assignee: Nanopoint, Inc., Honolulu, HI (US)

( * ) Notice: Subject to any disclaimer, the term of this patent is extended or adjusted under 35 U.S.C. 154(b) by 149 days.

(21) Appl. No.: 10/463,668

(22) Filed: Jun. 18, 2003

Related U.S. Application Data

(60) Provisional application No. 60/389,288, filed on Jun. 18, 2002.

(51) Int. Cl.
*G02F 1/03* (2006.01)
(52) U.S. Cl. .............. 250/458.1; 250/461.2; 250/459.1
(58) Field of Classification Search ............. 250/458.1, 250/459.1, 461.2, 306, 310
See application file for complete search history.

(56) References Cited

U.S. PATENT DOCUMENTS

| | | | |
|---|---|---|---|
| 5,004,307 A | | 4/1991 | Kino et al. |
| 6,208,886 B1 * | | 3/2001 | Alfano et al. ............... 600/473 |
| 6,818,907 B1 * | | 11/2004 | Stark ........................ 250/492.1 |
| 2003/0215844 A1 * | | 11/2003 | Chapsky et al. ................ 435/6 |

OTHER PUBLICATIONS

Milster et al.; *Super-Resolution by Combination of a Solid Immersion Lens and Aperture*; The Japanese Society of Applied Physics, Part 1, No. 3B: Mar. 2001.
Hecht et al.; *scanning near-field optical microscopy with aperture probes: Fundamentals and applications*; Special Topic: Near-field Microscopy and Spectroscopy: Journal of Chemical Physics; vol. 112, No. 18; May 8, 2000.
Betzig & Chichester; *Single Molecules Obseerved by Near-field Scanning Optical Microscopy*; Science, New Series; vol. 262, No. 5138, Nov. 26, 1993; pp. 1422-1425.
Mansfield & Kino; *Solid Immersion Microscope*; Appl. Physics Letter; vol. 57, No. 24, Dec. 10, 1990.
D. V. Palanker et al.; *On contrast parameters and topographic artifacts in near-field infrared microscopy*; Journal of Applied Physics, vol. 88, No. 11; Dec. 1, 2000.
Tom D. Milster et al.; *The Nature of the Coupling field in Optical Data Storage using Solid Immersion Lenses*; The Japanese Society of Applied Physics, Part 1, No. 3B; Mar. 1999.
Jonathan D. Bui et al.; *Probing intracellular dynamics in living cells with near-field optics*; Journal of Neuroscience Methods 89 (1999) 9-15; Feb. 27, 1999.

(Continued)

*Primary Examiner*—David Porta
*Assistant Examiner*—Faye Polyzos
(74) *Attorney, Agent, or Firm*—James Creighton Wray; Meera P. Narasimhan

(57) ABSTRACT

A method and apparatus for near-field intra-cellular apertureless tomographic imaging uses sub-wavelength nano-particle in a cell which generates tomographic projections. A detector detects and collects high-frequency details from evanescent field interactions of the nano-particle with surrounding molecules and provides near-field imagery of a cell volume. The detector may be a detector ring movably/pivotably disposed near the cell or it may be a discrete detector. The discrete detector may be coupled to a microscope with high NA objective coupled for minimizing solid angles of collected photons from each tomographic projection. A rotating platform may hold the cell substrate. The nano-particle is a sub-wavelength scattering fluorescent particle producing fluorescent rays that exit the cell and impinge on the detector. The tomographic projection provides tomographic views of molecules or cell structure with the help of the particle in the cell.

41 Claims, 2 Drawing Sheets

OTHER PUBLICATIONS

Tang et al.; *Consideration and control of writing conditions with a near-field APSIL probe*; Proceedings of International Symposium on Optical Memory and Optical Data Storage/ 2002; ISBN 0-7803-7379-0; Published:2002; pp. 243-245.

* cited by examiner

NEAR-FIELD INTRA-CELLULAR APERTURELESS TOMOGRAPHIC IMAGING

This application claims the benefit of U.S. Provisional Application No. 60/389,288, filed Jun. 18, 2002.

BACKGROUND OF THE INVENTION

The invention relates to micro-imaging and illuminating.

In micro imaging needs exist for small illuminating sources for precise illumination and imaging of bodies.

SUMMARY OF THE INVENTION

The invention particularly relates to a near-field tomographic imagery and illumination of cell volume similar to x-ray computed tomography (CT), where each tomographic projection contains high-frequency detail from evanescent field interactions with DNA molecules.

Scanning Near-Field Optical Microscope (SNOM) probes currently move over the surface of the object being measured. SNOM is an optical technique capable of resolving beyond the refraction limit. Resolutions in the 20 nanometer range have been demonstrated. SNOM technology is applied to cells and to plasma membranes. SNOM has the ability to study single molecules as well as macro-molecules such as DNA.

Fluorescent micro-particles used as Near-Field "flashlight" where sub-wavelength resolution images could be reconstructed of in situ gene conformation and acetylation status of histones at that site. In the infrared, the fluorescing beads are replaced with (or attached to) magnetic beads and maneuvered around the cell using magnetic field micro-manipulation or magnetic tweezers. The sub-wavelength size particle allows for the near-field interaction of an apertureless configuration.

The sub-wavelength scattering particles may be metallic spheres such as, but not limited to gold or silver, to enhance the evanescent field interactions with the molecules within living cells. Due to their plasma frequency, silver particles benefit from plasmon resonance enhancement in the visible region of the spectrum, while gold particles exhibit plasmon resonance in the infrared.

Mechanisms of gene silencing are poorly understood. Nuclear receptors bound by hormones are able to activate as well as to repress genes. The detailed mechanism of the signal transduction between the nuclear receptor and the RNA polymerase inside the nucleus remains unclear. There exists a need to penetrate a cell membrane and to image the inside of an intact cell for understanding the mechanisms underlying nuclear receptor action and providing novel insights into gene regulatory pathways.

Understanding of the mechanics of these processes at this resolution could provide a much better concept of gene expression and ultimately lead to a better understanding of cell replication, development, and differentiation as well as tumor formation and aging.

Needs exist for a system capable of collecting data from high-resolution imagery providing a unique imaging tool for the investigation of cells at the sub-cellular and molecular level.

If a cell population were treated with an inhibitor of histone deacetylase to induce a global increased acetylation of crucial lysines on histones in chromatin, it is possible to image the subsequent conformal changes that occur at the sites where previously silenced genes become activated. Fluorescent beads target fluorescently labeled genes that were silenced in an untreated sample, image the conformation of silenced genes in-situ in live cells, and compare the images with the untreated sample where the fluorescent genes of interest are now expressed.

In a preferred embodiment of the present invention, Near-Field Intra-Cellular Apertureless Tomographic Imaging (NICAT), a near-field imaging technique collects tomographic projections from a sub-wavelength fluorescent particle. A detector ring or microscope collects near-field tomographic projections of emitted light from within the cell. This technique provides higher resolution from existing imaging systems of living cells and provides a new tool for cell screening of various diseases.

Another preferred embodiment of the present invention uses a sub-wavelength scattering particle that is illuminated externally from the cell, which produces evanescent wave interactions in the region of the particle. This particle can be maneuvered around within the cell or attached to a specific gene or other molecule of interest.

These and further and other objects and features of the invention are apparent in the disclosure, which includes the above and ongoing written specification, with the claims and the drawings.

DETAILED DESCRIPTION OF PREFERRED EMBODIMENTS

A preferred embodiment, NICAT, collects near-field imagery of the cell volume similar to x-ray computed tomography (CT). Each tomographic projection produced by the present invention however, contains high-frequency detail from evanescent field interactions with sub-cellular molecules, such as but not limited to DNA.

Figure 1:
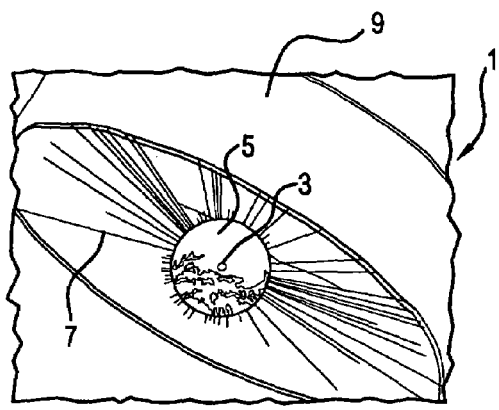
FIG. 1 is a perspective view of a computer model of NICAT, schematically showing a cell illuminated internally by fluorescing nano particle or particles, rays projected from the cell, and a detector ring.

Referring to FIG. 1, the computer model shows a perspective view of a NICAT system 1. A sub-wavelength nanoparticle 3, or particles or bead, is positioned within a single cell 5 fluoresces and produces rays 7 which exit the cell 5 and impinge on a movable detector ring 9. The detector ring 9 surrounds the single cell 5 which is illuminated from within by a fluorescent sub-wavelength particle or particles 3. The sub-wavelength particles may have particular affinity for molecules within the cell or receptors in a cell wall or may be attached to a delivery system for carrying the particles into the cells.

Figure 2:
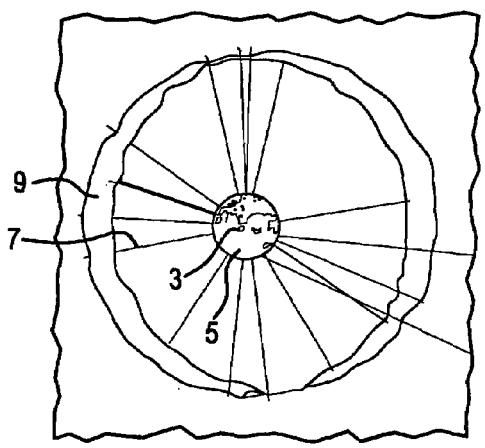
FIG. 2 is a end view of the computer model of the cell and rays in the NICAT system shown in FIG. 1.

Referring to FIG. 2, the computer model shows a top view of a NICAT detector ring 9, which surrounds a single cell 5 illuminated within, from a fluorescent particles or bead 3.

Figure 3:
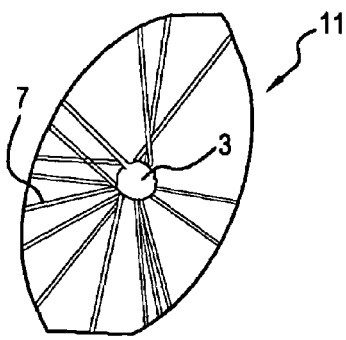
FIG. 3 is a computer model of a near-field flashlight showing illuminating with fluorescing particles in or on a cell.

Referring to FIG. 3, the computer model shows a near-field flashlight 11. The fluorescent particle 3 is less than the wavelength of emitted light 7 and produces near-field interactions with surrounding molecules. The preferred embodiment produces tomographic views of molecules or cell structure using the particle located within a cell. The near-field illuminator 11 may be an individual particle 3 or may have a fluorescent probe attached directly to an imaging site.

Figure 4:
FIG. 4 shows fluorescent nanoparticles imaging of mitotic cells.

Referring to FIG. 4, the NICAT system 1 captures a fluorescent image 13 of mitotic cells 15, which have absorbed some of fluorescent nano-particles 23. The mitotic cells in the confocal microscope image contain 100 nm fluorescent particles 17 in the medium 19. Some of the particles 23 have been "taken up" inside the cell membranes 25. The 100 nm particles are observable but not resolvable using far-field techniques.

Near-field affects are not limited to tapered fibers or sub-wavelength apertures, but can be realized using sub-wavelength self-emitting particles. The present technique is a method of collecting high-resolution evanescent wave information from a set of projections or viewing slices through a cell using a single particle as an internal light source similar to positron emission tomography (PET). However, in this arrangement, the NICAT system collects sub-wavelength spatial information in each near-field tomographic projection.

Figure 5:
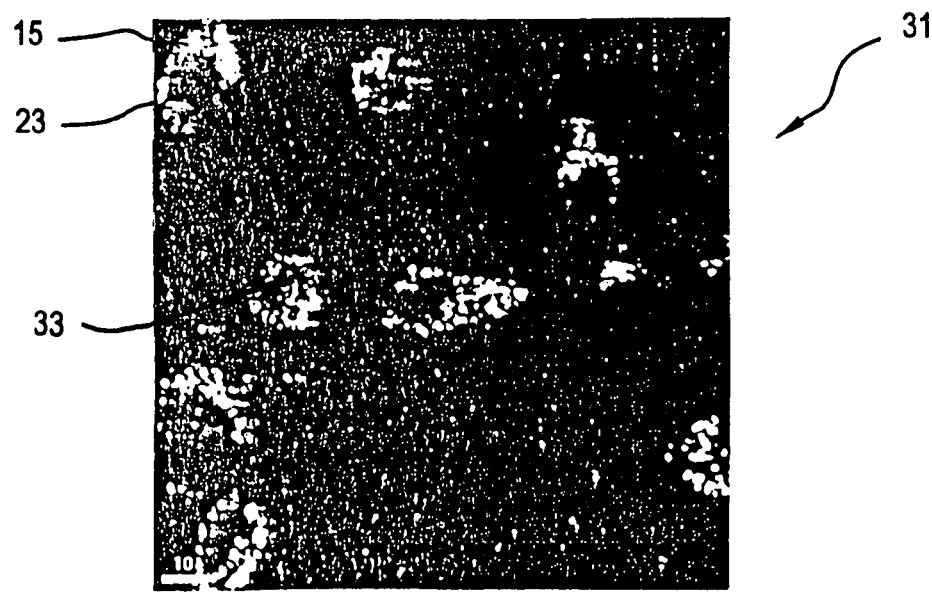
FIG. 5 is a confocal image of mitotic cells with internal fluorescent nano particle illumination.

FIG. 5 is a laser scanning confocal microscope image 31. Argon laser illumination at 488 nm produces a fluorescent excitation peak at 530 nm of the 100 nm fluorescent particles 23 in mitotic cells 15. A single particle 33 in the center of a cell 15 can provide full 4-pi steradian tomographic viewing. Multiple particles 23, as shown, can provide additional near-field information from multiple locations simultaneously.

In a preferred embodiment of the present invention, a fluorescent marker is attached to a specific gene site for localizing high-resolution imagery surrounding the molecule.

One embodiment of the present invention uses a sub-wavelength size scattering particle that is illuminated externally from the cell. That produces evanescent wave interactions in the region of the particle. The particle can be maneuvered around within the cell or attached to a specific gene or other molecule of interest.

The sub-wavelength scattering particles may be metallic spheres such as, but not limited to gold or silver, to enhance the evanescent field interactions with the molecules within living cells. Due to their plasma frequency, silver particles benefit from plasmon resonance enhancement in the visible region of the spectrum, while gold particles exhibit plasmon resonance in the infrared.

Figure 6:
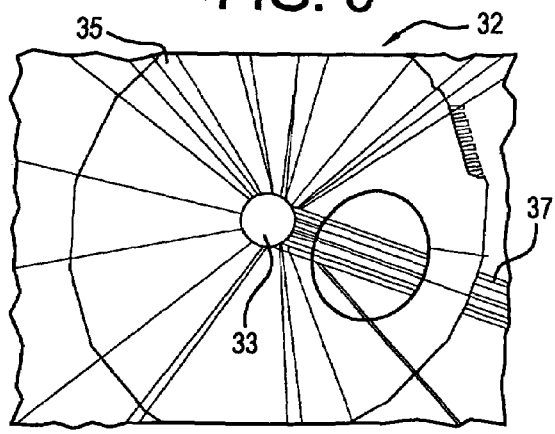
FIG. 6 is a computer model of near-field imaging using laser excitation, activation, or reflection from an internal nano particle.

Referring to FIG. 6, apertureless configuration 32 using far-field illumination of a sub-wavelength particle, which can be maneuvered around cell volume using laser or magnetic micromanipulation. The near-field scattering particle 43 can be raster scanned around the cell volume with magnetic or optical tweezers. Fluorescent micro-particles 33 are used as a Near-Field "flashlight" where sub-wavelength resolution images may be reconstructed from in-situ gene conformation and acetylation status of histones at that site. In the infrared, the fluorescing beads are replaced with, or attached to, magnetic beads and maneuvered around the cell using magnetic field micro-manipulation or magnetic tweezers.

The sub-wavelength size particle 33 allows for the near-field interaction of an apertureless configuration. This near-field imaging technique uses an apertureless configuration by illuminating a sub-wavelength particle 33 (in the far-field) or external to the cell 35.

Figure 7:
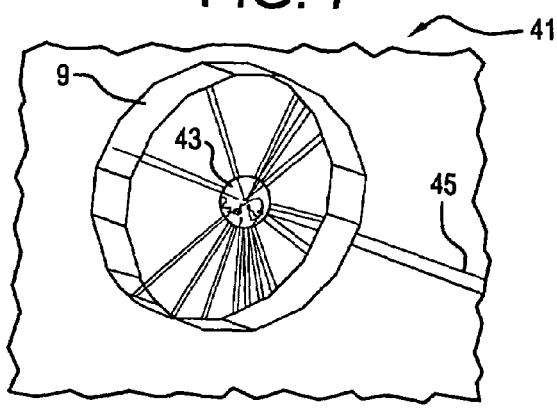
FIG. 7 is a near-field tomographic imaging system computer model similar to FIG. 6 showing far field illumination of a sub-wavelength scattering particles within a cell.

Referring to FIG. 7, the near-field scattering particle 43 can be raster scanned around the cell volume with magnetic or optical tweezers. FIG. 7 shows the near-field tomographic system 41 using far-field illumination 45 of a sub-wavelength scattering particle 43. Near-Field Computed Tomographic Imaging using far-field illumination is achieved with a detector ring 9 that pivots around the cell to collect tomographic projections. In one embodiment, a discrete detector coupled to a microscope with a high NA objective is used. The microscope minimizes the solid angle of the collected photons from each individual projection, and the cell substrate is mounted to a rotating platform.

While the invention has been described with reference to specific embodiments, modifications and variations of the invention may be constructed without departing from the scope of the invention, which is defined in the following claims.

We claim:

1. An apparatus for near-field intra-cellular apertureless tomographic imaging comprising a sub-wavelength nano-particle in a cell, an illuminator for illuminating the nano-particle, tomographic projection generated by the nano-particle, a detector for detecting and collecting high-frequency details from evanescent field interactions of the nano-particle with surrounding molecules and providing near-field imagery of a cell volume.

2. The apparatus of claim 1, wherein the detector comprises a detector ring disposed near the cell.

3. The apparatus of claim 2, wherein the detector ring is pivotable around the cell for collecting the tomographic projections.

4. The apparatus of claim 1, wherein the detector is a discrete detector.

5. The apparatus of claim 4, further comprising a microscope with high NA objective coupled to the discrete detector for minimizing solid angles of collected photons from the tomographic projection.

6. The apparatus of claim 5, further comprising a rotating platform, wherein a cell substrate with the cell is mounted to the rotating platform.

7. The apparatus of claim 1, wherein the nano-particle is a sub-wavelength scattering fluorescent particle producing fluorescent rays, wherein the fluorescent rays exit the cell and impinge on the detector.

8. The apparatus of claim 7, wherein the sub-wavelength particle has particular affinity for molecules within the cell or receptors in a wall of the cell.

9. The apparatus of claim 8, wherein the sub-wavelength particle is attached to a delivery system for being carried into the cell.

10. The apparatus of claim 7, wherein the particle is a fluorescent bead.

11. The apparatus of claim 7, wherein the particle forms a near-field flashlight.

12. The apparatus of claim 7, wherein the fluorescent particle is less than a wavelength of emitted light and produces near-field interactions with surrounding molecules.

13. The apparatus of claim 7, wherein the tomographic projection comprises tomographic views of molecules or cell structure provided by the particle in the cell.

14. The apparatus of claim 7, wherein the illuminator is a near-field illuminator or an individual particle or a fluorescent probe attached directly to an imaging site.

15. The apparatus of claim 7, wherein the imagery includes a fluorescent image of mitotic cells comprising the fluorescent particles.

16. The apparatus of claim 15, wherein the mitotic cells in a confocal microscope image comprise 100 nm fluorescent particles.

17. The apparatus of claim 16, further comprising particles taken-up inside cell membranes.

18. The apparatus of claim 7, wherein the nano-particle comprises sub-wavelength self-emitting particles.

19. The apparatus of claim 7, wherein the particle comprises a single particle in the cell providing full 4-pi steradian tomographic viewing.

20. The apparatus of claim 19, wherein the particle comprises multiple particles providing additional near-field information from multiple locations simultaneously.

21. The apparatus of claim 7, wherein the particle is a fluorescent marker attached to a specific gene site for localizing high-resolution imagery surrounding the molecules.

22. The apparatus of claim 7, wherein the sub-wavelength particle comprises metallic spheres for enhancing evanescent field interactions with the molecule in the cell.

23. The apparatus of claim 22, wherein the metallic spheres are gold or silver spheres.

24. The apparatus of claim 23, wherein silver particles have plasma frequencies for plasmon resonance enhancement in visible region of light spectrum.

25. The apparatus of claim 23, wherein the gold particles have plasma frequencies for plasmon resonance in an infrared region.

26. The apparatus of claim 1, wherein the molecules include DNA molecules.

27. The apparatus of claim 1, wherein the illuminator is a laser illuminator producing a fluorescent excitation peak of the fluorescent particles in the cell.

28. The apparatus of claim 1, further comprising a laser device for laser micromanipulation and maneuvering of the particle in the cell.

29. The apparatus of claim 1, further comprising a magnetic device for magnetic micromanipulation and maneuvering of the particle in the cell.

30. The apparatus of claim 1, further comprising magnetic or optical tweezers for raster scanning of the particle around the cell.

31. The apparatus of claim 1, wherein the imagery comprises sub-wavelength resolution images reconstructed from in-situ gene conformation and acetylation status of histones at that site.

32. The apparatus of claim 1, wherein the nano-particle comprises magnetic beads attached to fluorescent particles for detecting in infrared regions.

33. The apparatus of claim 1, wherein the nano-particle is a magnetic bead.

34. A method of collecting high-resolution evanescent wave information from a set of projections or viewing slices through a cell comprising disposing a nano-particle as an internal light source in a cell, illuminating the particle, providing tomographic projections, detecting and collecting information about the particle with a detector, and providing sub-wavelength spatial information in each near-field tomographic projection.

35. The method of claim 34, wherein the disposing the particle comprises disposing sub-wavelength scattering fluorescent particle in the cell.

36. The method of claim 35, wherein the detecting comprises detecting interaction of the particle with surrounding molecules and imaging the particle and the molecules.

37. The method of claim 35, wherein the disposing comprises disposing a single particle in a center of the cell and providing full 4-pi steradian tomographic viewing in the cell.

38. The method of claim 37, wherein the disposing comprises disposing multiple particles in the cell and providing additional near-field information from multiple locations simultaneously.

39. The method of claim 35, further comprising attaching a fluorescent marker a specific gene site and localizing high-resolution imagery surrounding the molecule.

40. The method of claim 35, further comprising illuminating the sub-wavelength scattering particle externally from the cell and producing evanescent wave interactions in regions of the particle.

41. The method of claim 35, further comprising maneuvering the particle around within the cell or attaching the particle to a specific gene or a molecule of interest and enabling near-field interaction of an apertureless configuration.

* * * * *